(12) United States Patent
Mawdsley et al.

(10) Patent No.: US 10,070,829 B2
(45) Date of Patent: Sep. 11, 2018

(54) SYSTEM AND METHOD FOR LOW X-RAY DOSE BREAST DENSITY EVALUATION

(71) Applicant: SUNNYBROOK RESEARCH INSTITUTE, Toronto (CA)

(72) Inventors: Gordon E. Mawdsley, Toronto (CA); Martin J. Yaffe, Toronto (CA); Oliver Alonzo-Proulx, Toronto (CA)

(73) Assignee: SUNNYBROOK RESEARCH INSTITUTE, Ontario (CA)

( * ) Notice: Subject to any disclaimer, the term of this patent is extended or adjusted under 35 U.S.C. 154(b) by 151 days.

(21) Appl. No.: 14/775,871

(22) PCT Filed: Mar. 14, 2014

(86) PCT No.: PCT/CA2014/050241
§ 371 (c)(1),
(2) Date: Sep. 14, 2015

(87) PCT Pub. No.: WO2014/138995
PCT Pub. Date: Sep. 18, 2014

(65) Prior Publication Data
US 2016/0029979 A1    Feb. 4, 2016

Related U.S. Application Data

(60) Provisional application No. 61/783,786, filed on Mar. 14, 2013.

(51) Int. Cl.
*A61B 6/04* (2006.01)
*A61B 6/00* (2006.01)

(52) U.S. Cl.
CPC ............ *A61B 6/0414* (2013.01); *A61B 6/502* (2013.01); *A61B 6/5217* (2013.01); *A61B 6/582* (2013.01); *A61B 6/583* (2013.01)

(58) Field of Classification Search
CPC ...... A61B 6/0414; A61B 6/0435; A61B 6/502
See application file for complete search history.

(56) References Cited

U.S. PATENT DOCUMENTS

| | | | | |
|---|---|---|---|---|
| 4,090,084 A | * | 5/1978 | Epstein | A61B 6/502 378/180 |
| 4,943,986 A | * | 7/1990 | Barbarisi | A61B 6/502 378/208 |

(Continued)

FOREIGN PATENT DOCUMENTS

FR    2832050    5/2003

OTHER PUBLICATIONS

The International Search Report and Written Opinion dated Jul. 8, 2014 for International Application No. PCT/CA2014/050241.

*Primary Examiner* — Thomas R Artman
(74) *Attorney, Agent, or Firm* — Quarles & Brady LLP

(57) ABSTRACT

A system and method for measuring volumetric breast density using a low dose of radiation are provided. This low-dose image can be added to a standard mammographic screening protocol with less than a two percent increase in radiation dose imparted to the subject. This low-dose image can also be used as a single standalone test to determine breast density for younger women for the purposes of risk determination or screening regimen planning. The breast density measurement is more accurate than measurements that can be obtained with existing systems and methods by making use of a compression assembly that maintains a parallel alignment between the compression paddle and breast support table. Additionally, the compression assembly maintains a uniform known thickness of the compressed breast. The system and method have the added benefit that they can be readily implemented on a conventional digital x-ray unit with low cost.

11 Claims, 5 Drawing Sheets

(56) References Cited

U.S. PATENT DOCUMENTS

| | | | | |
|---|---|---|---|---|
| 5,712,890 | A * | 1/1998 | Spivey | A61B 6/032 378/37 |
| 5,833,633 | A * | 11/1998 | Sarvazyan | A61B 1/0052 600/437 |
| 6,751,285 | B2 * | 6/2004 | Eberhard | A61B 6/502 378/37 |
| 7,873,198 | B2 * | 1/2011 | Shepherd | A61B 6/12 382/132 |
| 8,325,877 | B2 * | 12/2012 | Abenaim | A61B 6/502 378/37 |
| 8,942,342 | B2 * | 1/2015 | Abenaim | A61B 6/502 378/37 |
| 2003/0095624 | A1 * | 5/2003 | Eberhard | A61B 6/502 378/37 |
| 2005/0207528 | A1 * | 9/2005 | Hjarn | A61B 6/0414 378/37 |
| 2009/0003519 | A1 | 1/2009 | Defreitas et al. | |
| 2009/0076382 | A1 * | 3/2009 | Shepherd | A61B 6/12 600/426 |
| 2010/0166147 | A1 * | 7/2010 | Abenaim | A61B 6/502 378/63 |
| 2010/0331699 | A1 * | 12/2010 | Yu | A61B 8/0825 600/446 |
| 2011/0091011 | A1 * | 4/2011 | Abenaim | A61B 6/502 378/37 |
| 2011/0270079 | A1 * | 11/2011 | Osman | A61B 5/702 600/421 |
| 2013/0051520 | A1 | 2/2013 | Ramsauer | |
| 2015/0272535 | A1 * | 10/2015 | Joson | A61B 6/025 382/131 |

* cited by examiner

SYSTEM AND METHOD FOR LOW X-RAY DOSE BREAST DENSITY EVALUATION

CROSS-REFERENCE TO RELATED APPLICATIONS

This application represents the U.S. National Stage of International Application No. PCT/CA2014/050241, filed Mar. 14, 2014 which claims the benefit of U.S. Provisional Patent Application Ser. No. 61/783,786, filed on Mar. 14, 2013, and entitled "SYSTEM AND METHOD FOR LOW X-RAY DOSE BREAST DENSITY EVALUATION"

BACKGROUND OF THE INVENTION

The field of the invention is systems and methods for x-ray mammography. More particularly, the invention relates to systems and methods for estimating breast density from an x-ray mammogram.

Mammographic density, hereafter referred to as breast density, describes the relative amount of fibroglandular tissue in the breast compared to the total amount of breast tissue, which is mostly composed of fibroglandular tissue and fat or adipose tissue. Mammographic breast density has been identified as an independent risk factor for breast cancer, and studies have identified a 4-5 fold increase in risk for developing breast cancer in women with dense breast tissue versus women with less dense breast tissue (i.e., breast tissue with more fat). The addition of breast density quantification to mammographic examination has the potential to greatly improve the accuracy of breast cancer risk assessment, especially for those without hereditary or familial risk factors. The inclusion of accurate breast density measurements can also be potentially helpful for women by suggesting that other imaging modalities such as magnetic resonance imaging ("MRI") or ultrasound be used for initial screening instead of mammography because mammography's accuracy is known to be reduced in women with very dense breasts. Because the reporting of breast density is required in some jurisdictions, there is a desire to provide an accurate and reproducible quantitative density measurement method that is simple to implement on conventional digital mammography machines. To date, nearly all work in measuring breast density has used film-screen mammograms.

Quantitative methods, such as computer-assisted planimetry, can be very reproducible and are the best validated method for association with breast cancer risk, but they generally require at least some manual intervention and, thus, are time-consuming to use. With the increased utilization of digital mammography, automated computerized measurement of breast density is now becoming widely available, but has not yet been well validated. One major advantage of newer software methods applied to digital mammograms is that pixel signal levels can be measured objectively, yielding information about the composition of the breast tissue (e.g., volumetric breast density). The use of digital mammograms will allow automation and reduce variability. Automated breast density measurements that are both reproducible and demonstrated to be accurate could be an important addition to breast cancer risk assessment.

The current gold standard quantitative method of measuring breast density is the 2D Cumulus program developed by Dr. Martin Yaffe from Toronto. This method is a computer-assisted thresholding technique similar to planimetry. First, a film-screen mammogram is digitized. The pixels representing the total breast area and those representing dense breast area are then defined by a radiologist through an interactive program. The 2D Cumulus program yields the percent area density of a breast. There are, however, several limitations of the 2D Cumulus program.

The 2D Cumulus program uses binary information and a two-dimensional image of the breast. The binary nature of the procedure means that each pixel is counted as representing either one hundred percent breast tissue or one hundred percent fat, with no ability to represent a mixture of the two tissue types, or to account for the height of the column of tissue above the pixel. Furthermore, simple thresholding methods, such as 2D Cumulus, may cause dense tissue not to be included in the thin periphery of the breast, or may treat fatty tissue as being dense in regions where the compressed breast is thicker than average. Use of the 2D Cumulus program is also cumbersome, as it requires a radiologist or a trained scientist to visually select the division between fat and breast tissue, a process that can take as long as one minute per image. Because of these limitations, 2D Cumulus has only been used in the research setting and not in clinical practice.

For a risk model to be useful in clinical practice, breast density measurement should be automated, reproducible, accurate, precise, and, ideally, measured on a continuous scale. This eliminates observer bias and provides maximal discrimination.

The work of Shepherd, et al., (as described in U.S. Pat. Nos. 6,516,045; 6,654,445; and 7,873,198) calculates mass density, which is related to, but not equivalent to mammographic density. The process described by Shepherd requires that calibration materials of one-hundred percent fat and one-hundred percent glandular materials be placed on the breast support, and also requires that radio-opaque markers be present in each image to enable thickness measurements.

Standard compression methods for mammography use a movable, semi-rigid clear plastic compression paddle. The breast is placed on a bottom breast platform that is flat, and the paddle is then lowered onto the breast, usually while the technologist is holding the breast in place to ensure proper tissue coverage in the image receptor's field of view. A significant patient concern in mammography is the discomfort the patient feels when the breast is compressed with sufficient force to spread out the breast tissues. The reasons for using such high compression include: (1) to make the breast thinner and thereby reduce patient radiation exposure; (2) to improve image quality by reducing the amount of scattered radiation; (3) to make the breast more uniform in thickness in the direction of the x-ray flux, leading to a more uniform exposure over the entire breast image; (4) to immobilize the breast during the x-ray exposure, thereby reducing image blurring; and (5) to bring breast tissues out from the chest wall into the exposure area and thus image more tissue. A problem with the calculation of volumetric breast density is the requirement that thickness must be known accurately in order to relate the attenuation to a given mammographic density. For instance, two millimeters of error in the path length on the breast could result in an error of five percent or more in the breast density measurement.

On most mammography machines, the paddles and readout systems are not designed to produce uniform compression. All paddles show some deflection when compressed on a breast, often as much as 3 mm in the centre. They also deflect from front-to-back due to flexion of the mechanical components, which varies with the compression force. Some compression paddles also tilt, further introducing the possibility for variations in compressed breast thickness.

The electronic readout of thickness can be incorrectly calibrated, or the error may change with compression force applied. Even for those mammographic units that report thickness compensated for compression force, there can be errors as large as two millimeters. These errors can be much greater if the breast is not centered on the breast support plate. Calibrating for variations in thickness is time consuming, and not always accurate. As noted above, accurate measurement of compressed breast thickness is an important factor in determining breast density; however, the measurement of thickness provided by commercial mammography systems can differ by as much as one centimeter from the actual thickness due to deflection of the breast compression plate and the inaccuracies in the readout system.

Therefore, there remains a need to provide a system and method for quantifying volumetric breast density that can more accurately determine the thickness of the breast, thereby addressing the drawbacks of currently available methods.

SUMMARY OF THE INVENTION

The present invention overcomes the aforementioned drawbacks by providing a system and method for quantifying the proportion or density of a tissue using a lower level of compression force and a lower x-ray dose.

It is an aspect of the invention to provide a compression assembly for compressing a breast in use with a mammography system. The compression assembly includes a rigid plate and at least one spacer. The at least one spacer is coupled to the rigid plate and sized such that the spacer maintains the rigid plate in a substantially parallel alignment at a fixed distance from a breast support plate of an x-ray mammography system, thereby providing a region for receiving and compressing a breast at a substantially uniform thickness. The at least one spacer may be composed of a material having a known density and/or attenuation value.

It is another aspect of the invention to provide a method for measuring a density of a subject's breast with a mammography system. The method includes compressing the subject's breast to a defined uniform thickness using a rigid compression paddle that is parallel to a breast support plate and spaced apart from the breast support plate at a fixed distance by at least one spacer. Data is then acquired with the mammography system by exposing the compressed breast to x-rays that traverse the rigid compression paddle before traversing the compressed breast and impinging upon an image plane of an x-ray detector. Attenuation values are determined from the acquired data at all points in the image plane and are then converted to mammographic density values. Breast volume and volumetric density content are then estimated by calculating the total volume of dense tissue by summing the mammographic density values across the total volume of the breast, and dividing the total volume of dense tissue by the total volume of the breast.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Accurate breast density results are difficult to obtain, and the currently existing, non-automated methods for measuring breast density are very subjective. The currently existing automated techniques also have their problems, including a lack of accuracy when estimating breast thickness, and tilt and bulging of the compression paddle, which decrease the accuracy of breast thickness estimation. In addition, the conventional method requires that the patient receive a radiation dose that is equal to that from a standard mammographic exposure. This requirement reduces the likelihood that a density measurement would be made unless the patient was receiving a mammogram for another purpose.

The present invention provides a system and method for measuring volumetric breast density using a low dose of radiation. For instance, this low-dose image can be added to a standard mammographic screening protocol with less than a two percent increase in radiation dose imparted to the subject. If only a density measurement is performed, then the dose imparted to the subject is less than two percent of that imparted in a standard mammographic examination. The breast density measurement obtained with the present invention is more accurate than measurements that can be obtained with existing systems and methods. The present invention also has the added benefit that it can be readily implemented on a conventional digital x-ray unit with low cost.

The present invention is capable of self calibration using one or more objects having x-ray attenuation characteristics that are similar to those of breast tissue. These objects are used to establish the spacing between a compression paddle and a breast support, and can provide direct signal numbers representing those density values.

A calibration and correction for breast support deflection can also be added for different thickness breasts. This Feature can be achieved by compressing different size phantoms containing a homogeneous gel or liquid, and using the resultant image signal values to calculate the different path lengths through this material from that presented by a rigid flat phantom.

A breast compression assembly for use with an x-ray mammography system that is capable of compressing the breast to an accurate and constant thickness. This compression assembly may be attached to any mammography system, and can be used to accurately measure volumetric breast density using a low-dose x-ray exposure, as will be described below in more detail.

Figure 1:
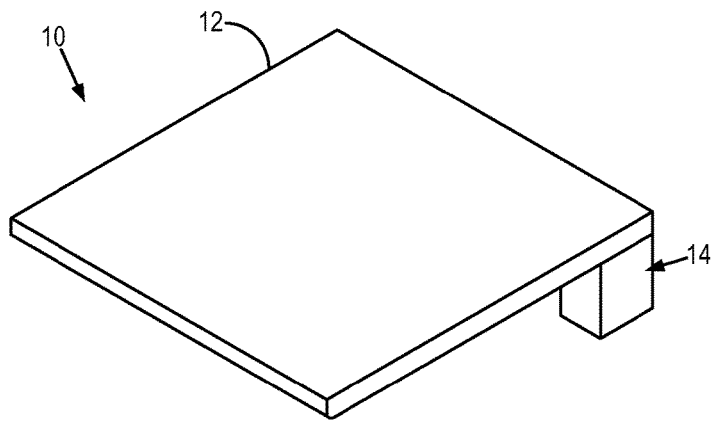
FIG. 1 is an example of one configuration of a compression assembly of the present invention.
Figure 2:
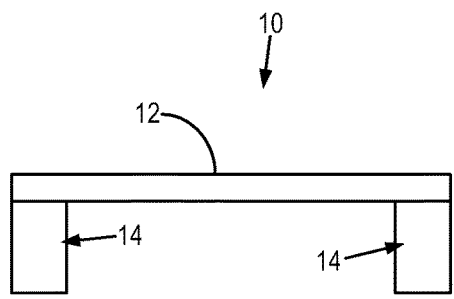
FIG. 2 is a front view of the compression assembly of FIG. 1.
Figure 3:
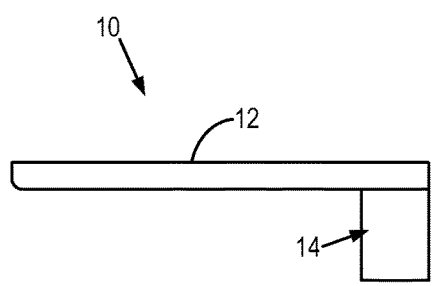
FIG. 3 is an elevational view of the compression assembly of FIG. 1.

With reference now to FIGS. 1-3, the compression assembly 10 of the present invention generally includes a paddle 12 and, optionally, one or more spacers 14. The compression assembly 10 can be a standalone device that is configured to be coupled to a mammography system, or the compression assembly 10 can be a device that is configured to be coupled to a breast compression paddle that forms a part of a commercially available mammography system. In the latter configuration, the compression assembly 10 of the present invention is configured to be coupled to the commercially available breast compression paddle using mechanical clips; self-adhering straps, such as hook-and-loop (Velcro™) strips; or so on. As an example, the compression assembly 10 can be configured to be coupled to the commercially available mammography system using the existing mounting hardware or mechanism available for that mammography system. In this way, the compression assembly 10 can be configured to be incorporated into pre-existing mammography systems without the need for specialized hardware.

The paddle 12 is generally a flat and rigid plate that is configured to be in parallel alignment with a breast support platform of a mammography system. Preferably, the paddle 12 is rounded on all edges that make contact with the patient to improve patient comfort. The paddle 12 may be composed of any suitable materials, but may preferably be composed of a transparent material to allow visual confirmation of the location of the patient's breast during mammographic examination. By way of example, the paddle 12 can be composed of clear poly(methyl methacrylate) ("PMMA"). Although one or more spacers 14 can be used to maintain the paddle 12 in parallel alignment with a breast support platform, other approaches for maintaining this parallelism can also be used. For instance, the mounting for the breast support plate can be modified such that it does not deflect more than one millimeter. As another example, parallel linkages or a straight line system could be used when coupling the paddle 12 and/or the breast support plate to the mammography system.

The paddle 12 is preferably about one centimeter thick, or more. This thickness is chosen such that the distortion of the paddle 12, the entrance exposure, and the dose imparted to the patient are all reduced relative to their values that would occur for the native compression paddles used in conventional mammography systems. For example, the paddle 12 is thick enough to reduce the entrance exposure to the breast to less than ten percent of the normal entrance exposure received in a regular examination. An example of a paddle 12 configuration that achieves this result is a paddle 12 composed of 2.54 centimeter (one inch) thick PMMA, which attenuates the incident x-rays by about ninety percent (for x-rays whose effective energy is 20 keV).

The thickness of the paddle 12 is also chosen to make the paddle 12 very rigid, unlike the 1.5-3 mm polycarbonate or PMMA compression paddles used in current mammography systems, which bulge and deflect during the compression of a patient's breast. In some configurations, the paddle 12 may be thinner than one centimeter. In these configurations, an increased amount of x-ray filtration in the x-ray tube port can be used to decrease the effective dose imparted to the patient's breast.

The thicker paddle 12 hardens the x-ray beam provided by the mammography system, and thus absorbs most of the lower energy photons. In addition, the thicker paddle 12 absorbs a significant amount of the primary radiation. The combination of the attenuation provided by the thick paddle 12 and the beam hardening enables the use of a similar time of exposure as used for conventional mammography while reducing the dose to less than two percent of the dose imparted in a conventional mammography examination. When added to a mammography study, total dose will thus be below the MQSA limit for all systems. Using the compression assembly 10 of the present invention, imaging may be carried out with increased kV relative to that used for conventional mammography. This increased kV further reduces the effective dose imparted to the breast.

In one configuration, the paddle 12 is configured to be coupled to an existing compression paddle of a mammography system. In another configuration, however, the paddle 12 is configured to replace the compression paddle on an existing mammography system in its entirety.

Figure 4:
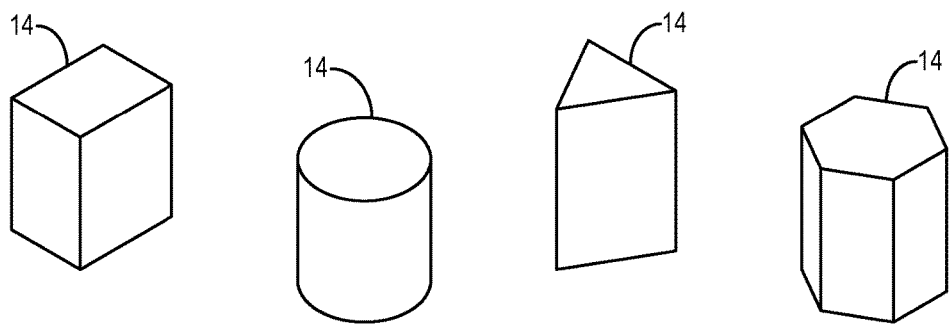
FIG. 4 is an illustration of different spacers that may form a part of the compression assembly of the present invention.

Preferably, the compression assembly 10 also includes one or more spacers 14. The spacers 14 can be coupled to the paddle 12 and positioned between the paddle 12 and the breast support plate of a mammography system. For example, the spacers 14 can be placed in or near the corners of the paddle 12 that are located away from the chest wall of the patient. The spacers 14 are sized to have a known thickness. By way of example, the spacers 14 can be constructed to have dimensions that differ by an integer number of centimeters, such as 2 cm×3 cm×4 cm, 4 cm×5 cm×6 cm, or 3 cm×5 cm×7 cm. The spacers 14 can be embedded with radioopaque or radiolucent materials so that their height can be identified on the images. For instance, the spacers 14 can be embedded with ball bearings that are arranged in a certain pattern that identifies the known height of the spacer 14. As illustrated in FIG. 4, however, the spacers 14 need not be rectangular, but can generally be constructed as having a cross-section of any suitable polygonal or otherwise arbitrary shape, including a circular cross-section, so long as the face of the spacer 14 that makes contact with the breast support plate 116 is parallel to the lower face of the paddle 12.

The spacers 14 are composed of a material with an attenuation equivalent to that of a breast tissue of known density. It is not necessary that the spacers 14 be composed of a material that mimics pure fat or pure fibroglandular tissue. When more than one spacer 14 is used, it may be preferable to have the different spacers 14 be composed of different materials. By having more than one material, the accuracy may be improved. A reference material, however, is not required because the spacers 14 provide an exact measurement of how thick the breast is under compression and of attenuation values.

Figure 5A:
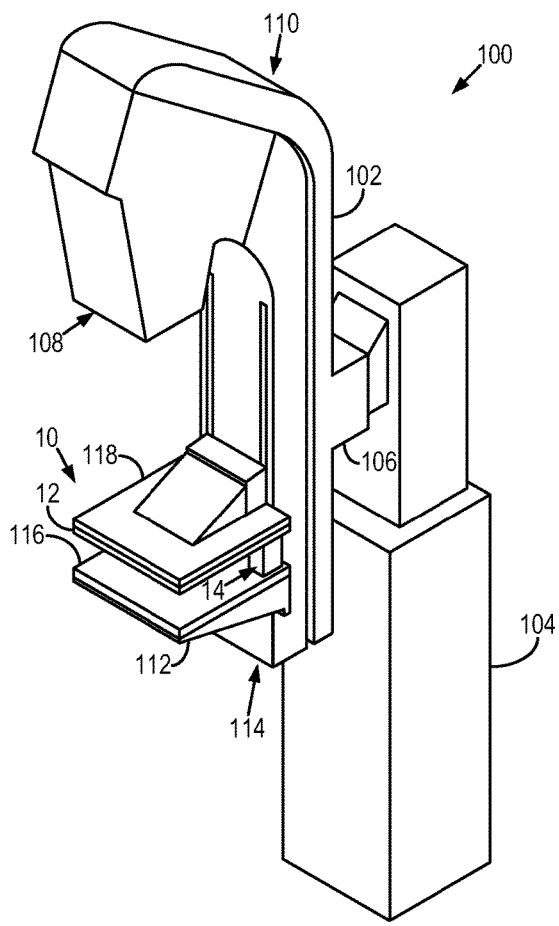
FIG. 5A is a mammography system incorporating one configuration of the compression assembly of the present invention.
Figure 5B:
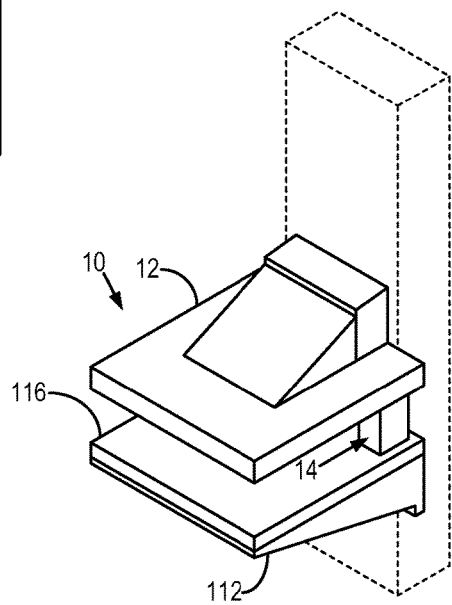
FIG. 5B is another configuration of the compression assembly of the present invention, which may form a part of a mammography system.

Referring now to FIG. 5A, the compression assembly 10 of the present invention can be implemented in an x-ray imaging system 100, such as a mammography system. The x-ray imaging system includes an arm 102 that is rotatably mounted to a base support 104 through a rotatable coupling 106. An x-ray source assembly 108 is coupled to a first end 110 of the arm 102, and an x-ray detector assembly 112 is coupled proximate an opposing end 114. The x-ray source assembly 108 extends substantially perpendicular to the arm 102 and is directed toward the x-ray detector assembly 112. The x-ray detector assembly 112 also extends from the arm 102 such that the x-ray detector assembly 112 receives x-ray radiation produced by the x-ray source assembly 108, transmitted through the breast, and incident on the x-ray detector assembly 112. A breast support plate 116, and a breast compression plate 118, are positioned between the x-ray source assembly 108 and the x-ray detector assembly 112. In this configuration, the compression assembly 10 is coupled to the existing breast compression plate 118 of the x-ray imaging system 100. The compression assembly 10, however, can also replace the breast compression plate 118, as illustrated in FIGS. 5B and 5C.

As discussed above, when the paddle 12 of the compression assembly 10 is sized to have a thickness less than one centimeter, additional filtering is preferably added to the x-ray source assembly 108 such that the mean glandular dose imparted to the breast is decreased.

Figure 5C:
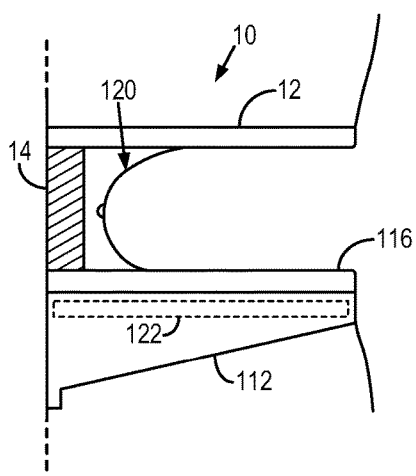
FIG. 5C is a schematic representation of a breast under compression with one configuration of the compression assembly of the present invention.

Referring now to FIG. 5C, the compression assembly 10 of the present invention is shown in use during a mammography session. The patient's breast 120 is positioned between the compression paddle 12 of the compression assembly 10 and the breast support plate 116 of the mammography system 100. One or more spacers 14 are also positioned between the compression paddle 12 and the breast support plate 116 such that, under compression, the breast 120 is maintained at a uniform and known thickness.

In operation, x-rays emitted by the x-ray source assembly 108 are attenuated by the compression assembly 10, the patient's breast 120, and the spacers 14 that form a part of the compression assembly 10. The attenuated x-rays are detected by an x-ray detector 122 in the x-ray detector assembly 112 as signals that represent transmission values, and can be converted to attenuation values at each pixel. For example, the transmission values can be converted to attenuation values by dividing the signal at each pixel by the average signal in a region outside of the breast, that is, a region in which primary radiation experiences little to no attenuation. The x-ray detector 122 may include any suitable x-ray detector, including an imaging plate, such as an accumulative phosphor sheet, or a flat panel detector, in which an array of x-ray detecting elements are arranged on an x-ray detection surface.

Because the compression paddle 12 is applied on the top of the breast 120, but supported by the spacers 14 with known dimensions, a uniform and known thickness of the breast 120 under compression is achieved. As an example, if the patient's breast thickness was measured to be 4.5 cm during a regular full-field digital mammography ("FFM"), then the compression paddle 12 can be positioned on top of the breast 120 and a set of 5.0 cm spacers 14 coupled underneath the compression paddle 12, or placed on top of the breast support plate 116. The compression paddle 12 is used to lightly compress the breast 120 against the breast support plate 116. For instance, the compression pressure will typically be below that used for current mammographic examinations.

When the compression paddle 12 is lowered to apply force to the breast 120, the compression paddle 12 becomes parallel to the breast support plate 116 and spaced apart from the breast support plate 116 by the height of the spacers 14, which in the example discussed here is 5.0 cm. With this geometry, the imaged breast 120 is slightly compressed to a constant thickness of 5.0 cm. The breast 120 can then be imaged using the same target, filter, kV, and closest mAs technique as used for the FFDM method. The volumetric breast density VBD of the breast 120 can then be accurately measured with calibrated data discussed below using the same algorithms as used on the high dose image. Breasts of other thicknesses will similarly be compressed using spacers 14 that are the next higher thickness than the thickness to which the breasts were compressed during the clinical mammogram.

Figure 6A:
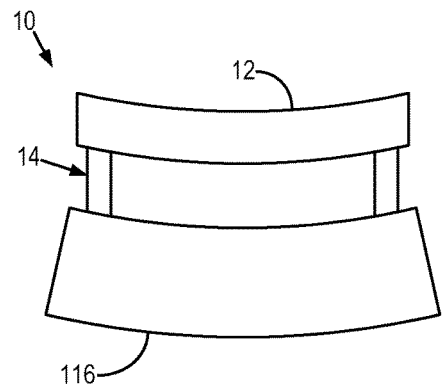
FIG. 6A is a configuration of the compression assembly of the present invention as used in a mammography system that implements a curved compression paddle and a curved breast support.
Figure 6B:
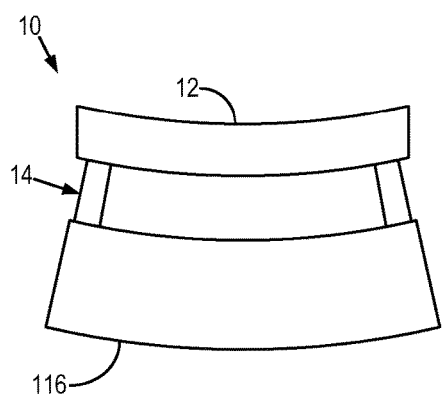
FIG. 6B is another configuration of the compression assembly of the present invention as used in a mammography system that implements a curved compression paddle and a curved breast support.

In some configurations, such as those illustrated in FIGS. 6A and 6B, the compression assembly 10 can be implemented in a mammography system that makes use of a compression paddle 12 and breast support 116 having curved surfaces. In these configurations, the contact faces of the spacers 14, which are the faces of the spacers 14 that make contract with the compression paddle 12 and the breast support 116, can be suitably curved so as to provide uniform contact with the compression paddle 12 and breast support 116. Accordingly, the contact faces of the spacers 14 may be suitably convex or concave. In this configuration, the spacers 14 are able to maintain the parallel relationship between the compression paddle 12 and breast support 116 such that the surfaces of the compression paddle 12 and breast support 116 are parallel curved surfaces.

Figure 7:
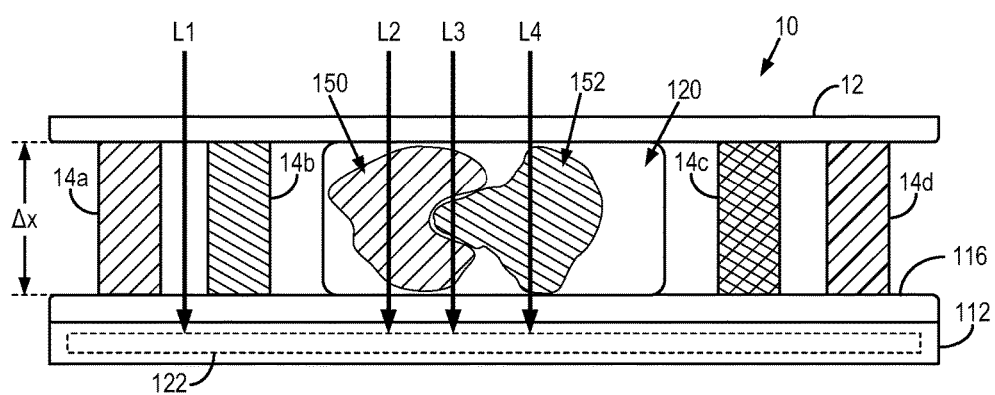
FIG. 7 is a schematic representation of a breast under compression, illustrating different x-ray beam paths through regions of uniform thickness, but different material compositions.

A digital mammography system can be characterized by measuring the effective attenuation of fat and glandular tissue for given tissue path lengths. The relationship of attenuation to tissue composition can be determined by calibrating the system using materials of known attenuation and known thicknesses. This can be achieved by using spacers 14 of known material composition and thicknesses, as illustrated in the example shown in FIG. 7. In this example, x-rays travelling along path L1 will pass through substantially only air, x-rays travelling along path L2 will pass through substantially only fat tissues in region 150 of the breast 120, x-rays travelling along path L3 will pass through an approximately 50-50 mixture of fat and fibroglandular tissue, and x-ray travelling along path L4 will pass through substantially only fibroglandular tissues in region 152 of the breast 120. By using the spacers 14 of in the compression assembly 10, each of the x-ray paths will traverse a similar, uniform path length, $\Delta x$.

To aid the calibration of the system, four spacers 14a, 14b, 14c, and 14d can be used in this example, each being composed of a different material having a known attenuation characteristic. For instance, spacer 14a can be composed of a material having attenuation characteristics similar to fat tissue, spacer 14b can be composed of a material having attenuation characteristics similar to fibroglandular tissue, spacer 14c can be composed of a material having attenuation characteristics similar to a mixture of fat and fibroglandular tissue, and spacer 14d can be composed of a material having attenuation characteristics similar to air. As an example, spacer 14c can be composed of a material having attenuation characteristics similar to a 50-50 mixture of fat and fibroglandular tissue.

A typical mammography system acquires a projection image of the compressed breast. Typically, two views are taken of each breast, one from above (cranial-caudal, or "CC") and one from the side (mediolateral-oblique, or "MLO"). In each view, the breast is compressed to reduce patient motion and scatter, separate overlapping structures in the breast, make the thickness of the imaged breast more uniform, and provide more uniform x-ray exposure. Using the compression assembly 10 of the present invention, an additional low-dose image is added for each breast. This low-dose image can be obtained in the CC view or MLO view. Two low-dose images, one in each of the CC view and the MLO view, can also be obtained. The positioning of the breast would be the same as for the full-dose mode except that the compression assembly 10 would be inserted before lightly compressing the breast for the low-dose image. The low-dose exposure is preferably taken at a fixed x-ray technique, but could also utilize a technique in which automatic exposure control is employed without impairing accuracy.

The linearity of pixel values reported by modern FFDM systems in arbitrary digital units ("ADU") per mAs is very stable. An mAs-normalized arbitrary digital unit ("NADU") is defined here to be the mean pixel value of a region-of-interest ("ROI") normalized by the mAs for the unprocessed ("RAW") digital image. When only air is imaged the NADU value is designated as $NADU_{air}$. For a given target, filter, kV, and thickness combination, attenuation, $\alpha$, can be defined as, $$\alpha = \frac{NADU}{NADU_{air}}. \tag{1}$$

Logarithmic attenuation can thus be defined as, $$LA = \log_{10}(\alpha) = \log_{10}\left(\frac{NADU}{NADU_{air}}\right). \tag{2}$$

In logarithmic space, the logarithmic attenuation of different breast density tissue is linear with respect to percentage of fibroglandular tissue ("PFG"), which is a measure of the proportion of fibroglandular tissue to the sum of fibroglandular and fatty tissue. That is to say, fatty tissue has a PFG of zero percent, an equal admixture of fatty tissue and fibroglandular tissue has a PFG of fifty percent, and fibroglandular tissue has a PFG of one hundred percent. A given FFDM system can be calibrated with potential combinations of target, filter, kV, and expected thicknesses. For each of these combinations, three PFG values (0, 50, 100) are measured with a block phantom, or the like.

An example of a calibration procedure includes obtaining measurements from a calibration phantom, such as a phantom that contains distinct regions of having different, known PFG values. Alternatively, the function of the calibration phantom can be replicated using appropriately configured spacers 14 in the compression assembly 10. For instance, the compression assembly 10 can be designed to include multiple spacers 14 having different, known PFG values. As an example, three different spacers 14 can be used, in which the spacers 14 would be designed to have PEG values of 0, 50, and 100. When the spacers 14 are present in a given image, they can be used as consistent calibration points. As an added advantage, due to the significant amount of beam hardening from the compression assembly 10, or added filtration, only a few calibration points are necessary to characterize the thickness-attenuation relationship.

Once the calibration is obtained, the effective attenuation of a breast can also be calculated from a single, low-dose image. With accurate knowledge of the breast thickness using the compression assembly 10 of the present invention, the amount and proportion of dense breast tissue, represented as volumetric breast density, can be determined from the low-dose image. The system of the present invention can thus be used to produce a report indicating breast density. This report can form a part of the patient's clinical record. By way of example, this report could be a DICOM structured report, or an HL7 report. In addition to calculating and reporting breast density, other quantitative metrics can also be determined and reported. For instance, the proportion of fibroglandular materials that define the breast can be calculated based on the summation of the attenuation values at the known compressed thickness of the breast. Also, the area of the breast that is making contact with the compression paddle 12 can be analyzed and an appropriate correction for thickness changes in the breast can be applied to regions outside the contact area.

Figure 8:
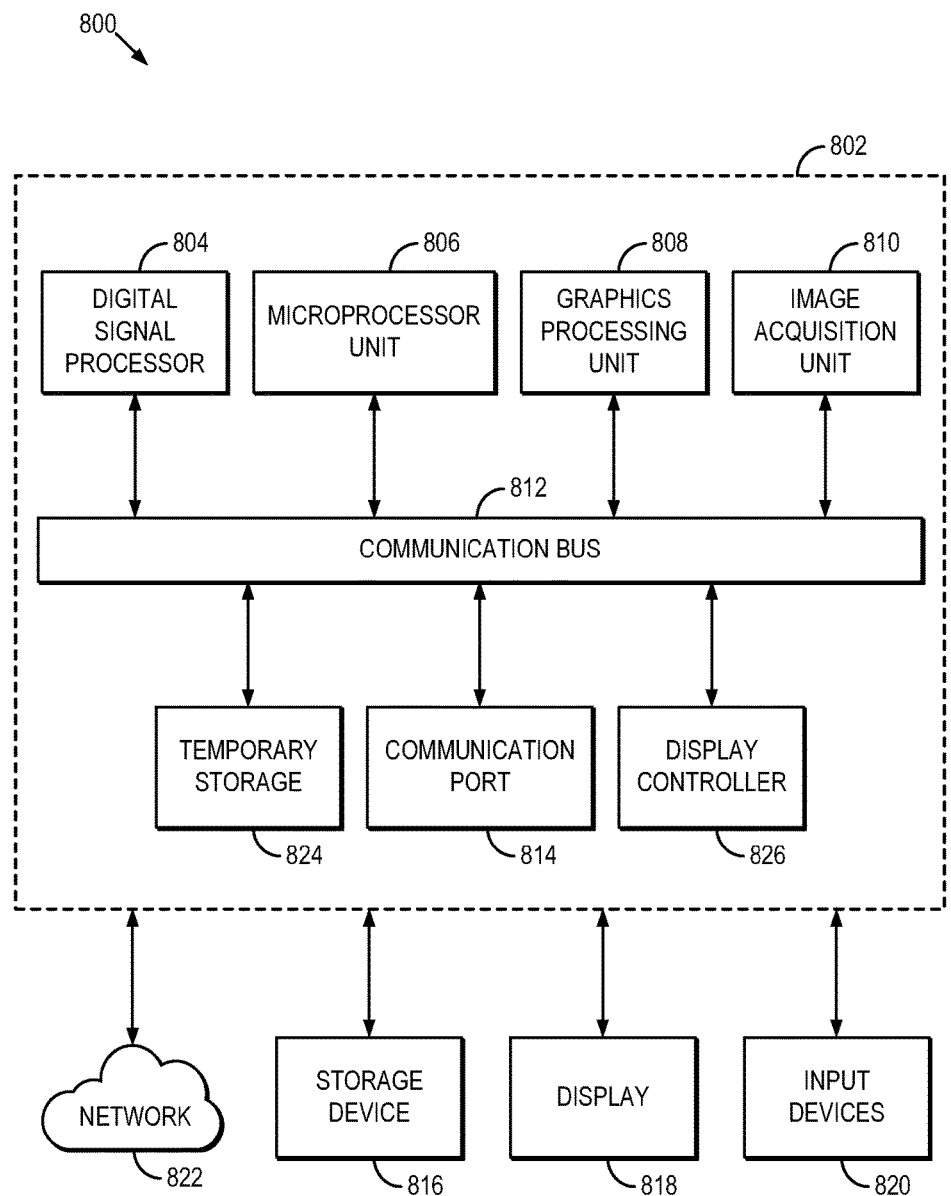
FIG. 8 is a block diagram of an example of a computer system that can be configured to implement some embodiments of the present invention.

Referring now to FIG. 8, a block diagram of an example computer system 800 that can be in communication with a mammography system, such as the mammography system illustrated in FIG. 5A, and configured or otherwise programmed to process medical images in accordance with embodiments of the invention described above. The image or images to be processed, which are preferably digital images, are provided to the computer system 800 by a mammography system, and are received in an image processing unit ("IPU") 802.

In some embodiments, the IPU 802 can include one or more processing units. As an example, the IPU 802 may include one or more of a digital signal processor ("DSP") 804, a microprocessor unit ("MPU") 806, and a graphics processing unit ("GPU") 808. The DSP 804, MPU 806, and GPU 808 can be any suitable, commercially available processor unit. The IPU 802 also preferably includes an image acquisition unit 810 that is configured to electronically receive an image to be processed. The DSP 804, MPU 806, GPU 808, and image acquisition unit 810 are all coupled to a communication bus 812. As an example, the communication bus 812 can be a group of wires or a hardwire used for switching data between the peripherals or between any component in the IPU 802.

The DSP 804 can be configured to receive an image and processes the image to yield a digital image. The MPU 806 and GPU 808 can be configured to process the image in conjunction with the DSP 804. As an example, the GPU 808 can process image graphics. Also as an example, the MPU 806 can be configured to control operation of components in the IPU 802 and can include instructions to perform processing of the image on the DSP 804.

In some embodiments, the DSP 804 can be configured to process an image received by the IPU 802 in accordance with the breast density estimation algorithms described herein. Thus, the DSP 804 can be configured to derive or otherwise compute breast density data, such as volumetric breast density measurements, from low-dose x-ray images.

The IPU 802 preferably includes a communication port 814 in electronic communication with other devices, which may include a storage device 816, a display 818, and one or more input devices 820. Examples of an input device 820 include, but are not limited to, a keyboard, a mouse, and a touch screen through which a user can provide an input.

The storage device 816 is configured to store digital images, whether those provided to the IPU 802 or those processed or enhanced images generated by the IPU 802. The display 818 is used to display images, such as images that may be stored in the storage device 816. Thus, in some embodiments, the storage device 816 and the display 818 can be used for displaying the digital image and for outputting other information.

The IPU 802 can also be in electronic communication with a network 822 to transmit and receive data, including images and reports using DICOM, XML, or other protocols. The communication port 814 can also be coupled to the IPU 802 through a switched central resource, for example the communication bus 812.

The IPU 802 can also include a temporary storage 824 and a display controller 826. As an example, the temporary storage 824 can store temporary information. For instance, the temporary storage 824 can be a random access memory.

Having described systems and methods that implement the present invention, generally, several non-limiting examples of the present invention in use are now provided.

EXAMPLE 1

Measuring Breast Density

In this example, the inventors demonstrate that breast density can be accurately measured under lower dose conditions than conventional mammography when implementing the systems and methods of the present invention.

In this example, thirty healthy volunteers and two women with previous surgery on a single breast were scanned using both a conventional, flexible mammogram paddle and the rigid paddle system described above. The mean age of the healthy volunteers was 63 years (50-81 yrs).

EXAMPLE 1

Materials and Methods

Each volunteer was scanned using a conventional four view screening mammogram using a flexible paddle. A technician arbitrarily selected the side to be imaged. The thickness of the compressed breast was determined by a technician from a crania-caudal ("CC") view of screen mammogram and the appropriately sized spacers were selected for a follow on scan using the rigid paddle system described above. The spacers were chosen to be either the same as the noted thickness (if an integer) or next centimeter higher. A low-dose image was then acquired using the rigid paddle system described above. In this example, the rigid paddle was 2.5 centimeters thick and composed of poly (methyl methacrylate) ("PMMA"). Images were acquired using a 35 kVp tube voltage setting, a 10 mAs setting, and with a Rhodium-Rhodium target-filter setup or a Molybdenum-Rhodium target-filter setup.

EXAMPLE 1

Results

Figure 9:
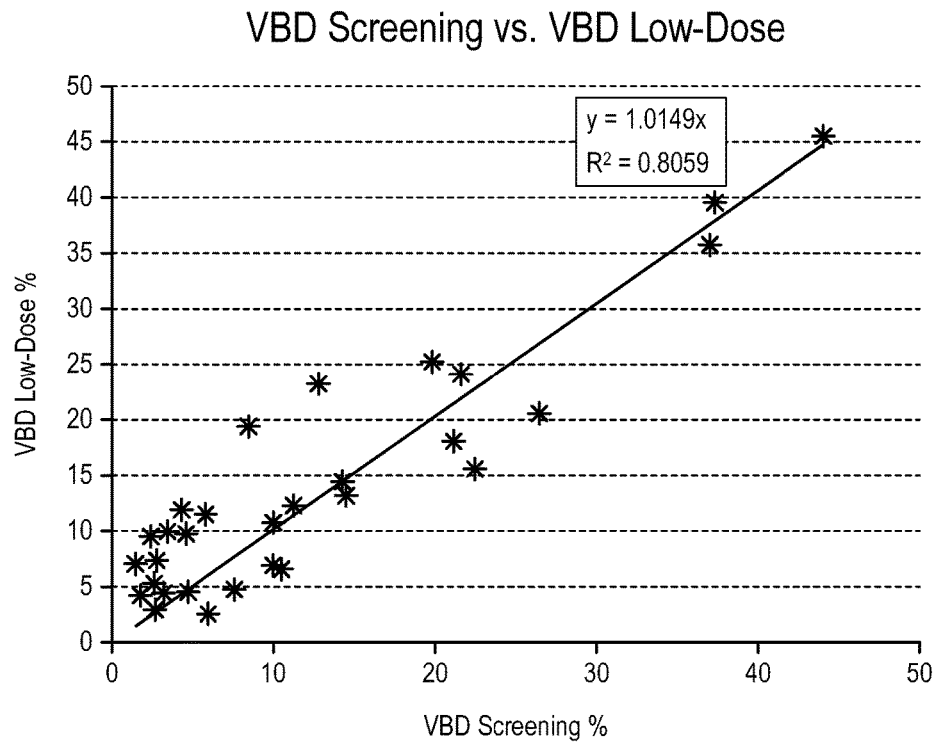
FIG. 9 is a plot showing a comparison between volumetric breast density values computed from conventional mammography images and from low-dose images in accordance with some embodiments of the present invention.

Images were automatically analyzed using the Cumulus Volume ("Cumulus V") program developed by Martin Yaffe at the University of Toronto. The resultant density was plotted with the screening image density derived from the conventional mammography images on the bottom axis and the low-dose density on the other axis, as seen in FIG. 9.

Figure 10:
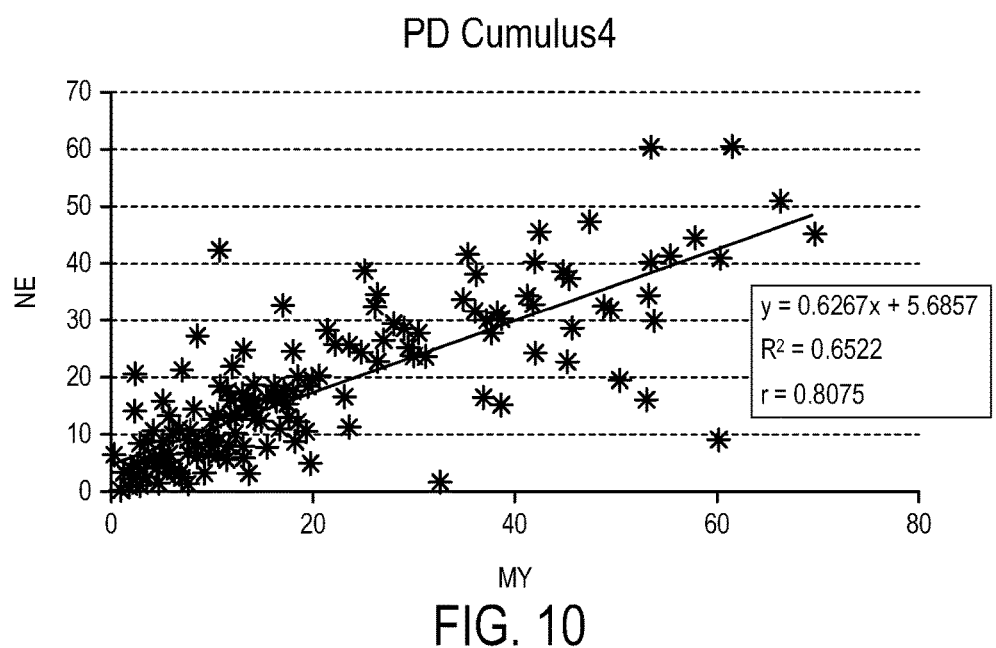
FIG. 10 is a plot showing a comparison between two human readers estimating breast density.

Two human readers ("NE" and "MY") analyzed area density and a comparison of their results are illustrated in FIG. 10. The R-value for the human readers is 0.81 as compared to the 0.90 achieved using the low-dose technique described herein, demonstrating that the method of the present invention is at least as reliable as using trained human estimators of breast density.

The low-dose volumetric density matches that obtained by using standard dose screening mammograms to within a few percent. The R-value is significantly better with the automatic technique than having humans read and score the images, however.

The present invention has been described in terms of one or more preferred embodiments, and it should be appreciated that many equivalents, alternatives, variations, and modifications, aside from those expressly stated, are possible and within the scope of the invention.

The invention claimed is:

1. A compression assembly for compressing a breast in use with a mammography system, comprising:
   a rigid plate; and
   at least one spacer coupled to the rigid plate and sized such that the spacer maintains the rigid plate in a substantially parallel alignment at a fixed distance from a breast support plate of an x-ray mammography system, thereby providing a region for receiving and compressing a breast at a substantially uniform thickness;
   wherein the rigid plate has a curved surface and the at least one spacer has a contact face that is curved so as to uniformly contact the curved surface of the rigid plate, thereby maintaining the rigid plate in a substantially parallel alignment at a fixed distance from a breast support plate of an x-ray mammography system.

2. The compression assembly as recited in claim 1 in which the at least one spacer comprises at least two spacers and each of the at least two spacers is composed of a different material having x-ray attenuation characteristics equivalent to a known composition of breast tissue.

3. The compression assembly as recited in claim 1 in which a thickness and a material of the rigid plate are chosen such that x-rays transmitted through the rigid plate are hardened sufficient to decrease a dose delivered to the compressed breast.

4. The compression assembly as recited in claim 3 in which the rigid plate is at least about one centimeter thick.

5. The compression assembly as recited in claim 1 in which the at least one spacer has a cross section that is polygonal.

6. The compression assembly as recited in claim 5 in which the cross section is at least one of square, rectangular, and circular.

7. The compression assembly as recited in claim 1 in which the at least one spacer is composed of a material having a known relationship to x-ray attenuation characteristics of breast tissue of a known composition.

8. The compression assembly as recited in claim 7 in which the at least one spacer is composed of a material having a known x-ray attenuation.

9. The compression assembly as recited in claim 8 in which the known attenuation is selected as equivalent to at least one of fat tissue, fibroglandular tissue, and combinations thereof.

10. The compression assembly as recited in claim 1 in which the at least one spacer is composed of a plurality of different materials, each of the plurality of different materials having a known relationship to x-ray attenuation characteristics of breast tissue of a known composition.

11. The compression assembly as recited in claim 10 in which the at least one spacer is composed of a plurality of materials, each of the plurality of materials having a known x-ray attenuation.

\* \* \* \* \*

UNITED STATES PATENT AND TRADEMARK OFFICE
CERTIFICATE OF CORRECTION

PATENT NO. : 10,070,829 B2
APPLICATION NO. : 14/775871
DATED : September 11, 2018
INVENTOR(S) : Gordon E. Mawdsley et al.

Page 1 of 1

It is certified that error appears in the above-identified patent and that said Letters Patent is hereby corrected as shown below:

In the Specification

Column 5, Line 9, "Feature" should be --feature--.

Column 7, Line 1, "FIG. SA" should be --FIG. 5A--.

Column 7, Line 59, "("FFM")" should be --("FFDM")--.

Column 9, Line 58, "PEG" should be --PFG--.

Column 11, Line 40, "carnia-caudal" should be --cranio-caudal--.

Signed and Sealed this
Thirteenth Day of November, 2018

Andrei Iancu
*Director of the United States Patent and Trademark Office*